(12) United States Patent
Ricciardi et al.

(10) Patent No.: US 10,596,289 B1
(45) Date of Patent: Mar. 24, 2020

(54) PIVOTING CABLE HOLDER FOR MULTI-FUNCTION DISINFECTION CABINET

(71) Applicants: Carl L. Ricciardi, Tomahawk, WI (US); Jonathan J. Ricciardi, Wausau, WI (US); Jonathan D. Yoder, Goshen, IN (US); Jim Gerend, Cedar Grove, WI (US); Dean Kreider, Cedarburg, WI (US)

(72) Inventors: Carl L. Ricciardi, Tomahawk, WI (US); Jonathan J. Ricciardi, Wausau, WI (US); Jonathan D. Yoder, Goshen, IN (US); Jim Gerend, Cedar Grove, WI (US); Dean Kreider, Cedarburg, WI (US)

( * ) Notice: Subject to any disclaimer, the term of this patent is extended or adjusted under 35 U.S.C. 154(b) by 0 days.

(21) Appl. No.: 16/132,561

(22) Filed: Sep. 17, 2018

Related U.S. Application Data

(63) Continuation-in-part of application No. 15/947,896, filed on Apr. 9, 2018.

(60) Provisional application No. 62/483,486, filed on Apr. 10, 2017.

(51) Int. Cl.
| | |
|---|---|
| *A61L 2/24* | (2006.01) |
| *A61L 2/22* | (2006.01) |
| *A61L 2/20* | (2006.01) |
| *A61L 2/02* | (2006.01) |

(52) U.S. Cl.
CPC ............. *A61L 2/24* (2013.01); *A61L 2/022* (2013.01); *A61L 2/208* (2013.01); *A61L 2/22* (2013.01); *A61L 2202/122* (2013.01); *A61L 2202/14* (2013.01)

(58) Field of Classification Search
CPC . A61L 2/0082; A61L 2/06; A61L 2/14; A61L 2/16; A61L 2/20; A61L 2/24; A61L 2/122; A61L 2/17; A61L 2/26
See application file for complete search history.

(56) References Cited

U.S. PATENT DOCUMENTS

| | | | |
|---|---|---|---|
| 3,893,843 A | * | 7/1975 | Fry .................... A47L 15/30 134/10 |
| 8,062,590 B1 | | 11/2011 | Ricciardi et al. |

(Continued)

*Primary Examiner* — Sean E Conley
*Assistant Examiner* — Brendan A Hensel
(74) *Attorney, Agent, or Firm* — Donald J. Ersler

(57) ABSTRACT

A multi-function product disinfection cabinet preferably includes a sealed test cabinet, a high level disinfection system, a dehumidifier and an electrical function tester. The sealed test cabinet preferably includes a sealed test chamber, a rear dehumidifier chamber and a rear droplet chamber. The high level disinfection system includes an aerosol blower, an aerosol generator and an aerosol control module. The aerosol blower blows a disinfectant from the aerosol generator into the disinfection chamber. A pivoting cable holder for a multi-function disinfection cabinet preferably includes a pivoting cable tube, a mounting bracket, a motor with gear reduction, a motor controller and two snap switches. The mounting bracket is attached to an outside sidewall of a disinfection chamber. The pivoting cable tube rotates in the disinfection chamber. The motor rotates the pivoting cable tube. The motor controller and two snap switches are used to control directional rotation of the motor.

20 Claims, 8 Drawing Sheets

(56) References Cited

U.S. PATENT DOCUMENTS

| | | | | |
|---|---|---|---|---|
| 8,506,900 B1* | 8/2013 | Ricciardi | ................ | A61L 2/04<br>422/292 |
| 2010/0316527 A1* | 12/2010 | McLaren | ................ | A61L 2/208<br>422/22 |

* cited by examiner

PIVOTING CABLE HOLDER FOR MULTI-FUNCTION DISINFECTION CABINET

CROSS-REFERENCES TO RELATED APPLICATIONS

This is a continuation-in-part application, which claims priority from application Ser. No. 15/947,896 filed on Apr. 9, 2018, which claims the benefit of provisional application No. 62/483,486 filed on Apr. 10, 2017.

BACKGROUND OF THE INVENTION

Field of the Invention

The present invention relates generally to the cleaning, sanitization, disinfection, high level disinfection of pathogenic contaminated patient monitoring equipment and more specifically to a multi-function surface treatment and/or surface cleaning chamber and/or enclosure, and even more specifically to a multi-function product sanitization, disinfection, and/or sterilization cabinet, which allows for preferably, but not limited to, low temperature decontamination, sanitization, disinfection or sterilization of products such as, but not limited to medical equipment and/or their various components and electrical testing of these same products and/or various components while achieving, without limitation, a greater than 6 log reduction of bio burden in less than 10 minutes. More generally, the present invention relates to an apparatus that can not only treat the surfaces of various object(s), components, and equipment, in a manner to achieve a result on their surfaces such as, but not limited to, sanitization, disinfection, and/or sterilization, but also effectively test the one or more object(s), such as, component(s), instrument(s) and/or equipment(s), for their effective function and performance, and more particularly any optical, physical, mechanical, and/or electrical function(s) and performance(s), at any time before, during, and/or after, any part of any surface treatment or decontamination cycle.

Discussion of the Prior Art

It appears that the prior art does not teach or suggest a multi-function product disinfection cabinet, which allows for low temperature disinfection of medical equipment that can achieve a greater than 6 log reduction in less than 10 minutes. More Specifically, the prior art does not teach or suggest a multi-function surface treatment enclosure that can clean, sanitize, disinfect, or sterilize the surfaces of any object and then test and check its function and/or performance before, during, and/or after their various surfaces are treated or decontaminated. In the clinical health care setting, certain instruments, diagnostic tools, and monitoring accessories, are essential for routine patient care. Generally, they are high-use, high-touch medical products and are constructed of materials that are not safe for high temperature disinfection methods including autoclaving. Because of their material makeup and dimensions they are not regularly cleaned sufficiently to eliminate cross-contamination from one patient to the next. The current method of cleaning by hand using strong chemicals tends to degrade the protective coating of the medical products.

In addition, patient monitoring leads, probes, sensors and instruments routinely fail through repeated use, hand cleaning, abuse, mishandling, and stress. If this condition is not timely diagnosed, these instruments can be transferred from room to room, patient to patient, until eventually diagnosed and identified as defective. Inventory, storage, and availability are major considerations in busy clinical treatment areas.

Recent published scientific literature has shown that antibiotic resistant pathogenic bio-burden including, but not limited to Super Bugs, is found primarily in the hospital and clinic setting. Further, there is an unanimity of thought within the medical community, that the transmission of infectious disease is spread from patient to patient by many vectors including improperly disinfected equipment. Because many of the serious diseases are spread by the hands of health care workers and by the patient touching the surfaces in his/her immediate vicinity as well as bowel and bladder function, perspiration, coughing or sneezing, it is paramount that all surfaces of patient related equipment are disinfected including the patient monitoring products that have been in direct patient contact.

Trial and error is a common approach to selecting suitable/reliable cable and/or wire leads, probes and devices. Currently, lacking a comprehensive methodology for disinfection, storage and grouping of like devices, hospitals have adopted a variety of less than optimal, methods for inventory control, testing, and securing replacement of items. This function usually defaults to the clinical end user at the most inopportune or inconvenient time.

Most hospitals have trained biomedical technicians that can be dispatched on an as needed basis to assist in troubleshooting patient monitoring equipment issues, but unavailability and prior commitment usually forces users to borrow the needed components from available sources creating inventory confusion and uncertainty as to the cleanliness, function, performance, and safety of the equipment.

This practice often results in questionable or defective items remaining in clinical areas available for others to use without knowing the component(s) functional condition or if it had been evaluated for electrical safety and whether it had been effectively disinfected. Often times clinical accessory items cannot be determined to be acceptable or unacceptable based on visual inspections alone. When defective items are inter-mixed with good items, the patient is put at risk for electrical injury and/or contamination. Troubleshooting various medical components, in clinical areas with limited availability of appropriate test equipment, resources, or skills, can impact diagnosis and timeliness of patient treatment. Sophisticated electronic test equipment necessary to diagnose electronic failure is not available in the area where these devices are routinely used.

Having convenient and timely access to fully tested and disinfected medical equipment probes, and accessories, will greatly improve the quality and safety to both patients and clinical operators. The diagnosis and removal of defective and contaminated equipment will reduce the risk of an electrical injury and pathogenic contamination. Having the items disinfected adds a level of protection against possible cross contamination from previous use on infected patients.

Manual cleaning and checking of the wire and cable leads and probes is often times inconsistent, inadequate and/or incomplete. A system whereby having high-usage reusable components tagged, tracked, function tested, disinfected, and inventoried will greatly improve work flow and operations in the clinical setting. U.S. Pat. No. 8,062,590 to Ricciardi et al. discloses methods and apparatuses for applying agent to objects.

Accordingly, there is a clearly felt need in the art for a multi-function product disinfection cabinet, which allows for low temperature disinfection of medical equipment, combined with electrical evaluation.

SUMMARY OF THE INVENTION

The present invention provides a multi-function surface treatment enclosure that can both clean, sanitize, disinfect, or sterilize, surfaces of any object intended for use in the health care industry, and then test, qualify, benchmark, and/or check, its function, status, and/or performance. Any effective means, process, and/or technology known to those skilled in the art can be used to clean, sanitize, disinfect, and/or sterilize, (Herein called "Decontaminate") the one or more of any targeted surfaces and/or treated object surfaces, within the one or more of any treatment enclosure(s), cabinet(s), and/or chamber(s), such as, but not limited to any, UV light, vaporized hydrogen peroxide, Peroxyacetic Acid (PAA) gas, any chemical agent in aerosol form, and/or any chemical agent in gas or vapor form. The multi-function product disinfection cabinet allows for low temperature disinfection of medical equipment capable of achieving at least a 6 log reduction of the most difficult to kill bio burden in less than 10 minutes.

The multi-function product disinfection cabinet preferably includes a sealed test cabinet, a high level disinfection system, a dehumidifier, at least one filter, an electrical function tester, a wireless control interface, a bar code reader, compliance reporting software and tracking software. The sealed test cabinet preferably includes a sealed test chamber, a top equipment space, a bottom equipment space, a rear dehumidifier chamber and a rear droplet chamber. The high level disinfection system includes an aerosol blower, an aerosol generator, aerosol tubing and an aerosol control module. U.S. Pat. No. 9,551,996 to Baumgartner et al. describes the elements of the aerosol generator and is herein incorporated by reference in its entirety. An inlet of the aerosol blower communicates with the sealed test chamber and an outlet of the aerosol blower is connected to an inlet of the aerosol generator. The aerosol blower blows air into the inlet of the aerosol generator and may also assist in drawing disinfectant aerosol from the reservoir of disinfectant. An inlet of the aerosol tubing is connected to an outlet of the aerosol generator and an outlet of the aerosol tubing communicates with the sealed test chamber. The aerosol control module controls the operation of the components of the high level disinfectant system. The high level disinfection system is preferably located in the top equipment space.

The dehumidifier preferably includes an evaporator coil 60, a condenser coil and an air conditioning compressor. An outlet of the air conditioning compressor is connected to an inlet of the evaporator coil. The air conditioner compressor pumps refrigerant through the evaporator coil and the condenser coil. The evaporator coil is located inside the dehumidifier chamber. The condenser coil is located in the droplet chamber. The air conditioning compressor is preferably located inside the bottom equipment space. Moisture in the air condenses on the evaporator coil and then drops into a liquid collection bottle. The at least one filter includes filtering of any airborne particles, vapors, or gases. A diverter valve is located in the bottom equipment chamber. The diverter valve includes a humidifier chamber inlet, a droplet inlet and outlet. The diverter valve shuttles between the humidifier chamber inlet and the droplet inlet. The outlet of the diverter valve is connected to an inlet of an air blower. An outlet of the air blower is coupled to a diffuser. The diffuser is located in a bottom of the sealed test chamber. Air blowing upward from the diffuser dries the products disinfected and tested in the sealed test chamber. The air from the diffuser passes through a dehumidifier screen and a droplet screen near at top of the sealed test chamber. The air travels through the humidifier and droplet screens into the rear dehumidifier chamber and the rear droplet chamber.

A disinfectant reservoir and a water reservoir are preferably located in the top equipment space. Disinfectant from the disinfectant reservoir flows into a first inlet of a mixing device and water from the water reservoir flows into a second inlet of the mixing device. An output of the mixing device is connected to the supply reservoir of the aerosol generator. The disinfectant reservoir and the water reservoir may be filed through a fill port located outside the sealed test cabinet. Inlets in a drain manifold draw liquid from numerous places in the sealed test cabinet and an outlet feeds the liquid into a liquid collection bottle. The liquid collection bottle is preferably removed from a front of the sealed test cabinet. The aerosol control module includes the electronic devices and software needed to control the operation of the disinfection system, dehumidifier and communicates with the electrical function tester. The wireless control interface preferably controls the operation of the aerosol control module through a touch screen interface. The wireless control interface includes wireless communication through Bluetooth and WIFI protocols.

An electrical function tester preferably includes an electronic test module, a plurality of test sockets, a plurality of interface test blocks and a bar code reader. The electronic test module includes the compliance software, the tracking software and the software to inventory tested electrical cables or components and reports testing compliance connected to one of the plurality of test sockets. The bar code reader is used to read a bar code, radio frequency identification tag, or other electronically imbedded coding circuit, which is used to identify each electrical cable or component placed in the testing disinfection chamber. The output of the bar code reader is connected to the electronic test module. The plurality of interface test blocks include but are not limited to: an ECG interface test block, a SPO2 interface test block, a IBP interface test block, a TEMP interface test block and a TOCO interface test block. Each interface test block preferably includes a base portion and an extension portion, which extends from the base portion. When needed, the interface test block will include a patient simulation device for providing feedback to a sensor of a particular cable. A plurality of connector pins extends from a back of the base portion. The connector pins are plugged into one of the plurality of test sockets. One end of an electrical cable is plugged into the base portion and an opposing end of the electrical cable is connected to the extension portion. The interface test blocks may also be permanently mounted in the sealed test chamber. The electrical function tester also tests the safety of the electrical cable. The electronic test module is located in the top equipment space.

A pivoting cable holder for a multi-function disinfection cabinet (pivoting cable holder) preferably includes a pivoting cable tube, a mounting bracket, a motor with gear reduction, a motor controller and two snap switches. The pivoting cable tube preferably includes a tubular rod, a first mounting rod, a second mounting rod, a first plurality of V-shaped members and a second plurality of V-shaped members. A bottom of the first plurality of V-shaped members are welded to a first mounting rod. The first mounting rod is welded to the tubular rod. A bottom of the second plurality of V-shaped members are welded to a second mounting rod. The second mounting rod is welded to the tubular rod, such that the first plurality of V-shaped members are located 180 degrees or opposite from the second plurality of V-shaped members. The mounting bracket includes a base member, a first leg, a second leg, a first switch plate and a second switch plate. The first leg extends outward from a first end of the base member and the second leg extends outward from a second end of the base member. The first switch plate extends outward from one side of the first leg and the second switch plate extends from an opposite side of the first leg.

A disinfection cabinet includes a disinfection chamber. The disinfection chamber includes opposing side walls. The pivoting cable tube is pivotally retained on opposing side walls with a pair of flanged bearing blocks. Tube holes are formed through the opposing side walls to receive the tubular rod. The pair of flanged bearing blocks are preferably retained on outside surfaces of the opposing side walls. First and second snap switches are attached to the first and second switch plates. The motor with gear reduction is attached to the base member of the mounting bracket with fasteners. An output shaft of the motor with gear reduction is inserted into an end of the tubular rod. A threaded hole is formed through an end of the tubular rod. A set screw is threaded into the threaded hole. The set screw is long enough to extend outward from an outer diameter of the pivoting cable tube.

A clockwise DPDT relay and a counter clockwise DPDT relay are used to provide power to a motor of the motor with gear reduction. The motor controller includes two output terminals, which output a clockwise voltage and a counter clockwise voltage. The clockwise voltage is outputted for a first period of time and the counter clockwise voltage is outputted for a second period of time. The clockwise voltage is used to energize a clockwise solenoid of the clockwise DPDT relay, which closes a first contact to supply a positive terminal of the motor with the clockwise voltage and a second contact to provide a ground path for a ground terminal of the motor. The pivoting cable tube rotates in a clockwise direction, until the setscrew forces the normally closed first snap switch to open. The opening of the first snap switch stops rotation of the pivoting cable tube. After the first period of time is over, the motor controller outputs the counter clockwise voltage for a second period of time. The counter clockwise voltage is used to energize a counter clockwise solenoid of the counter clockwise DPDT relay, which closes a first contact to supply a negative terminal of the motor with counter clockwise voltage and a second contact to provide a ground path for a positive terminal of the motor. The pivoting cable tube rotates in a counter clockwise direction, until the setscrew forces the normally closed second snap switch to open. The opening of the second snap switch stops rotation of the pivoting cable tube. After the second period of time is over, the motor controller outputs the clockwise voltage for a new first period of time. Each ultrasonic probe includes an ultrasonic head, a handle and a cord.

Typically, only the ultrasonic head and the handle are disinfected, which leaves the cord untreated. The pivoting cable holder allows the entire ultrasonic probe to be disinfected. The cord is placed between two adjacent V-shaped members of the pivoting cable tube, such that a longer portion of the cord extends from one side of the V-shaped members and the ultrasonic head and handle extend from an opposing side of the V-shaped members. The disinfection process includes a disinfection period, when the ultrasonic probe is treated with a disinfection aerosol and a drying stage when the disinfection aerosol is dried from the ultrasonic probe. The pivoting cable holder is preferably rotated 180 degrees to expose an untreated area of the cord that is retained between the two adjacent V-shaped members and also to dry an area of the cord that is retained between the two adjacent V-shaped members.

Accordingly, it is an object of the present invention to provide a multi-function product disinfection cabinet, which provides low temperature disinfection of medical equipment.

It is another object of the present invention to provide a multi-function product disinfection cabinet, which provides electrical and safety testing of electrical cables and other medical equipment.

Finally, it is another object of the present invention to provide a pivoting cable holder for a multi-function disinfection cabinet, which treats the entire surface area of an ultrasonic probe or electric device.

These and additional objects, advantages, features and benefits of the present invention will become apparent from the following specification.

DETAILED DESCRIPTION OF THE PREFERRED EMBODIMENTS

Figure 1:
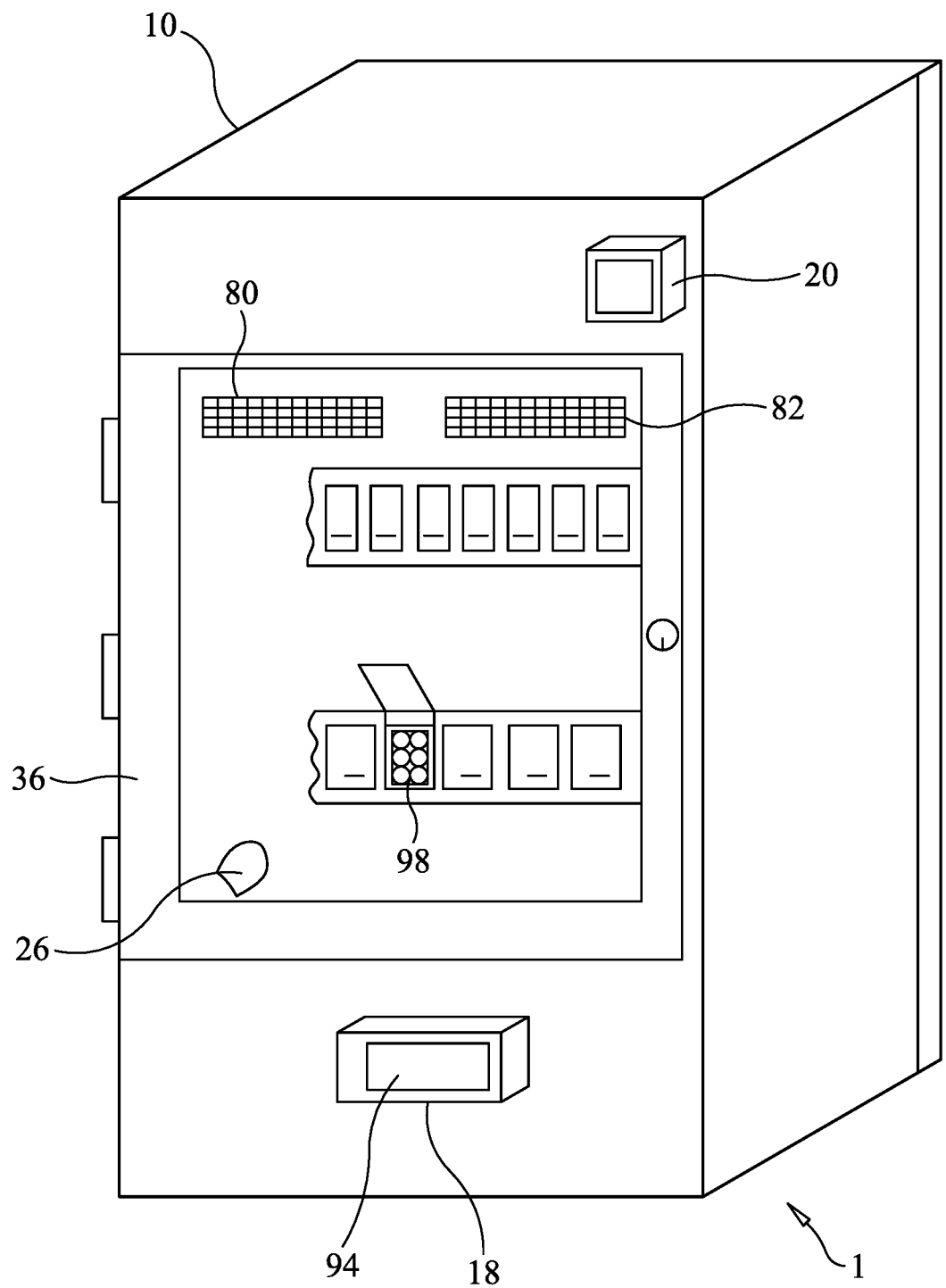
FIG. 1 is a perspective view of a multi-function product disinfection cabinet in accordance with the present invention.
Figure 2:
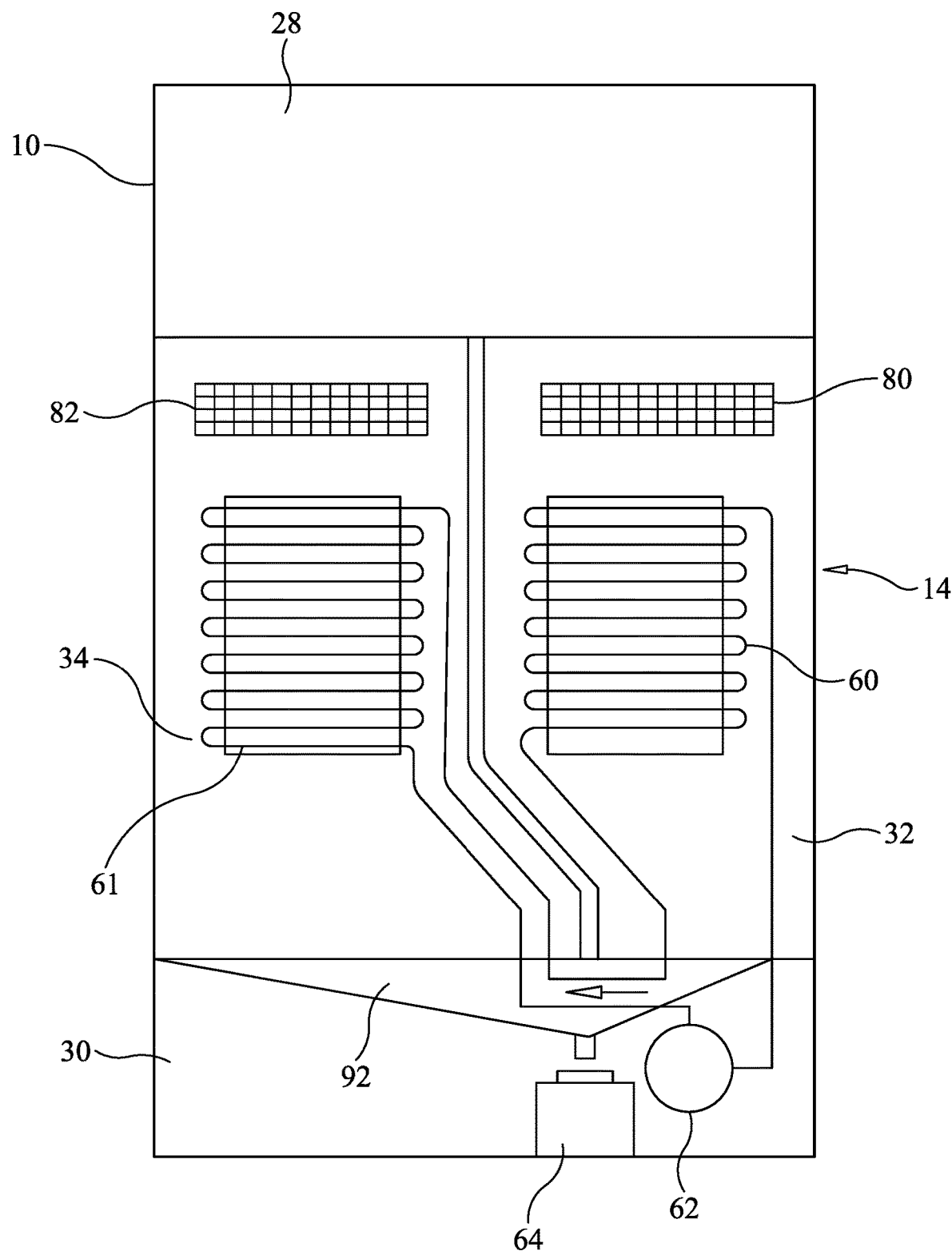
FIG. 2 is a rear view of a multi-function product disinfection cabinet with a rear panel removed to reveal a rear dehumidifier chamber and a rear droplet chamber in accordance with the present invention.
Figure 3:
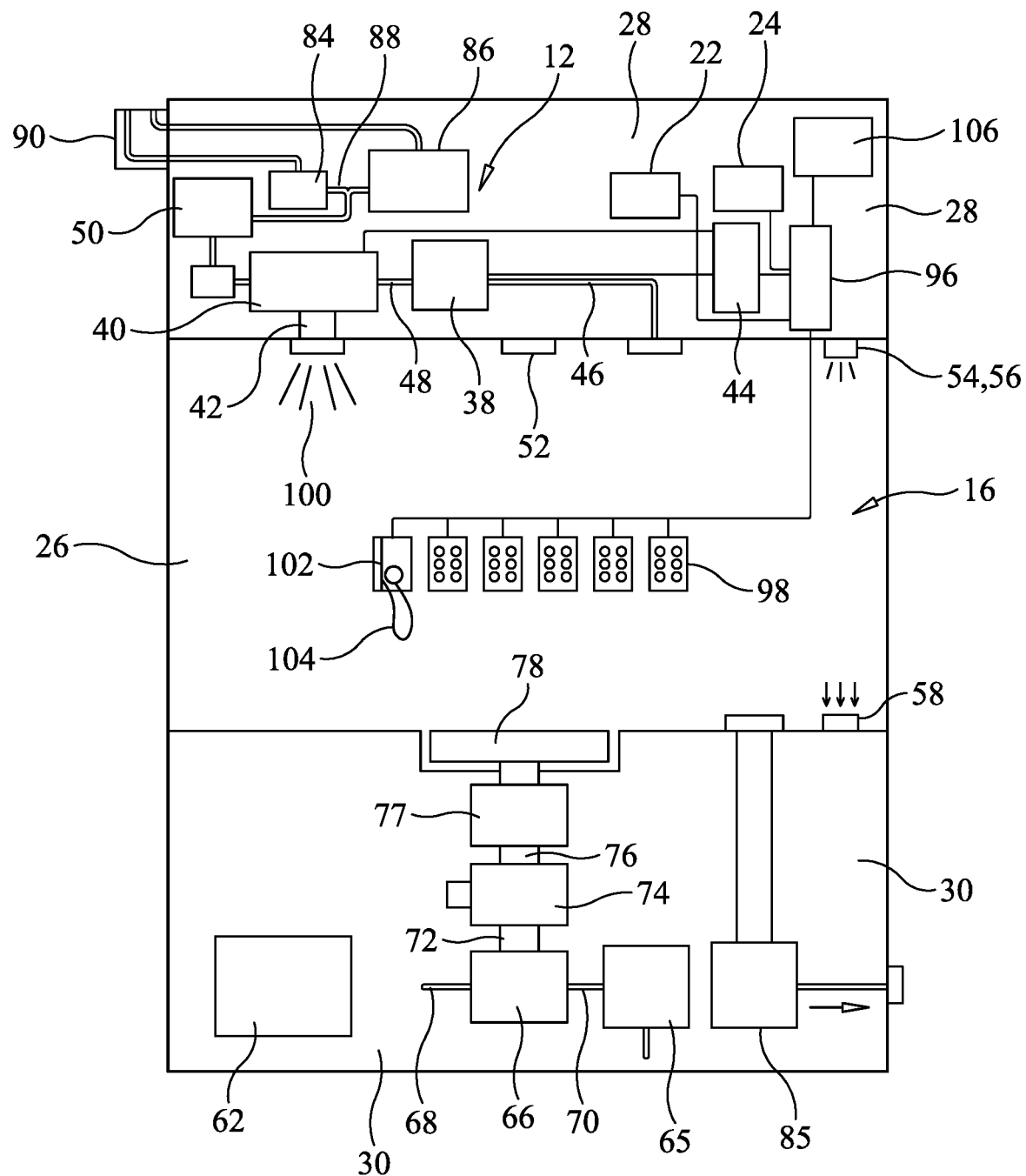
FIG. 3 is a schematic diagram of a portion of a multi-function product disinfection cabinet in accordance with the present invention.

With reference now to the drawings, and particularly to FIG. 1, there is shown a perspective view of a multi-function product disinfection cabinet 1. With reference to FIGS. 2-3, the multi-function product disinfection cabinet 1 preferably includes a sealed test cabinet 10, a high level disinfection system 12, a dehumidifier 14, an electrical function tester 16, a wireless control interface 18, a bar code reader 20, compliance reporting software 22 and tracking software 24. The sealed test cabinet 10 preferably includes a sealed test chamber 26, a top equipment space 28, a bottom equipment space 30, a rear dehumidifier chamber 32, a rear droplet chamber 34 and a sealed door 36.

The high level disinfection system 12 includes an aerosol blower 38, an aerosol generator 40, aerosol tubing 42 and an aerosol control module 44. U.S. Pat. No. 9,551,996 to Baumgartner et al. describes the elements of the aerosol generator 40 and is herein incorporated by reference in its entirety. An inlet 46 of the aerosol blower 38 communicates with the sealed test chamber 26 and an outlet 48 of the aerosol blower 38 is connected to an outlet of the aerosol generator 40. The aerosol blower 38 blows air into the inlet of the aerosol generator 40 and may also assists in drawing disinfectant aerosol 100 from the reservoir of disinfectant 50. The aerosol 100 includes a droplet size, which is preferably less than 0.7 microns. An inlet of the aerosol tubing 42 is connected to an outlet of the aerosol generator and an outlet of the aerosol tubing 42 communicates with the sealed test chamber 26. The aerosol control module 44 controls the operation of the components of the high level disinfectant system 12. The high level disinfection system 12 is preferably located in the top equipment space 28. It is preferable to have a light 52 to illuminate some types of disinfectant in the sealed test chamber 26. It is also preferable to have a light sensor 54 inside the sealed test chamber 26. The light sensor 54 includes a light source 56 and a light sensor 58. Light is emitted from the light source 56 and received by the light sensor 56 if no disinfectant or an insufficient amount of disinfectant is in the sealed test chamber 26.

The dehumidifier 14 preferably includes an evaporator coil 60, a condenser coil 61 and an air conditioning compressor 62. An outlet of the air conditioning compressor 62 is connected to an inlet of the evaporator coil 60. An outlet of the evaporator coil 60 is connected to an inlet of the condenser coil 61. An outlet of the condenser coil 61 is connected to an inlet of the air conditioner compressor 62. The air conditioner compressor 62 pumps refrigerant through the evaporator coil 60 and the condenser coil 61. The evaporator coil 60 is located inside the dehumidifier chamber 32. The condenser coil is located in the droplet chamber 34. The air conditioning compressor 62 is preferably located inside the bottom equipment space 30. Moisture in the air condenses on the evaporator coil 60 and then drops into a liquid collection bottle 64. Heat from the condenser coil 61 dries air going through the droplet chamber. A filtration unit 65 receives air from the droplet chamber 34. The air from the droplet chamber passes through the filtration unit 65. A diverter valve 66 is preferably located in the bottom equipment chamber 28. The diverter valve 66 includes a humidifier chamber inlet 68, a droplet chamber inlet 70 and an outlet 72. The diverter valve 66 shuttles between the humidifier chamber inlet 68 and the droplet chamber inlet 70. The outlet 72 of the diverter valve 66 is connected to an inlet of an air blower 74. An outlet 76 of the air blower 76 is connected to a heater 77. The heater 77 is connected to a diffuser 78. The diffuser 78 is preferably located in a bottom of the sealed test chamber 26. Air blowing upward from the diffuser 78 dries the products disinfected and tested in the sealed test chamber 26. The air from the diffuser 78 passes through a humidifier screen 80 and a droplet screen 82 near a top of the sealed test chamber 26. The air travels through the humidifier screen 80 into the dehumidifier chamber 32 and the droplet screen 82 into the droplet chamber 34. A vacuum pump 85 is preferably used to pull a vacuum on the sealed test chamber 26 before treatment of an electrical cable or component. The heater 77 may be used to remove any additional moisture not removed by the vacuum pump 85 in the sealed test chamber 26.

A disinfectant reservoir 84 and a water reservoir 86 are preferably located in the top equipment space 28. Disinfectant from the disinfectant reservoir 84 flows into a first inlet of a mixing device 88 and water from the water reservoir 86 flows into a second inlet of the mixing device 88. An outlet of the mixing device 88 is connected to the supply reservoir 50 of the aerosol generator 40. The disinfectant reservoir 84 and the water reservoir 86 may be filed through a fill port 90 outside the sealed test cabinet 10. Inlets (not shown) in a drain manifold 92 draw liquid from numerous places in the sealed test cabinet 10 and an outlet feeds the liquid into the liquid collection bottle 64. The liquid collection bottle 64 is preferably removed from a front of the sealed test cabinet 10. The aerosol control module 44 includes electronic devices needed to control the operation of the disinfection system 12, the dehumidifier 14 and communicates with an electronic test module 96 of the electrical function tester 16. The wireless control interface 18 preferably controls the operation of the aerosol control module 44 through a touch screen interface 94. The aerosol control module 44 preferably controls the electronic test module 96. The wireless control interface 18 includes wireless communication through Bluetooth and WIFI protocols.

The electrical function tester 16 preferably includes the electronic test module 96, a plurality of test sockets 98, a plurality of interface test blocks 102 and the bar code reader 20. The electronic test module 96 includes the compliance software 22, the tracking software 24 and software to inventory tested electrical cables or components and report compliance connected to one of the plurality of test sockets 98. An electrical cable 104 is retained in the interface test block 102. The interface test blocks 102 may be permanently electrically connected to electronic test module without the need for test sockets 98. The bar code reader 20 is used to read a bar code, radio frequency identification tag, or other electronically imbedded coding circuit, which is used to identify each electrical cable or component placed in the sealed test chamber 26. An output of the bar code reader 20 is connected to the electronic test module 96.

Figure 4:
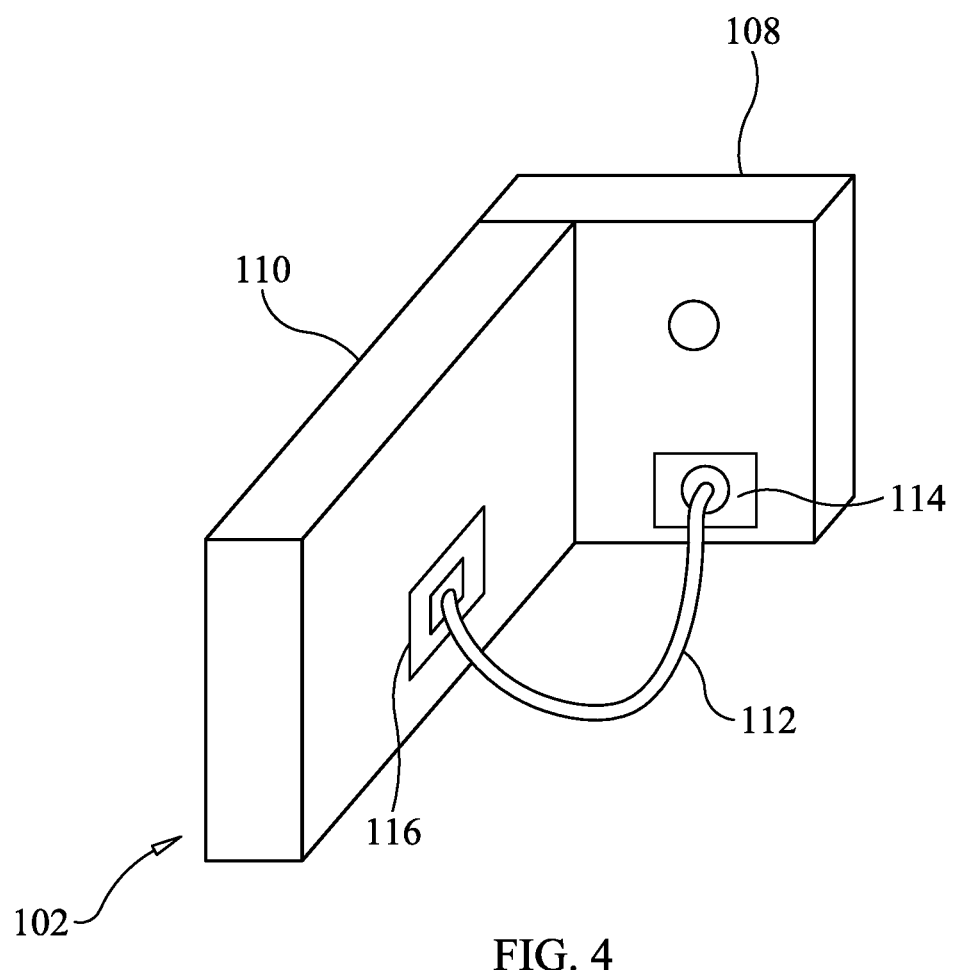
FIG. 4 is a perspective view of an interface test block with a cable inserted for testing in accordance with the present invention.
Figure 5:
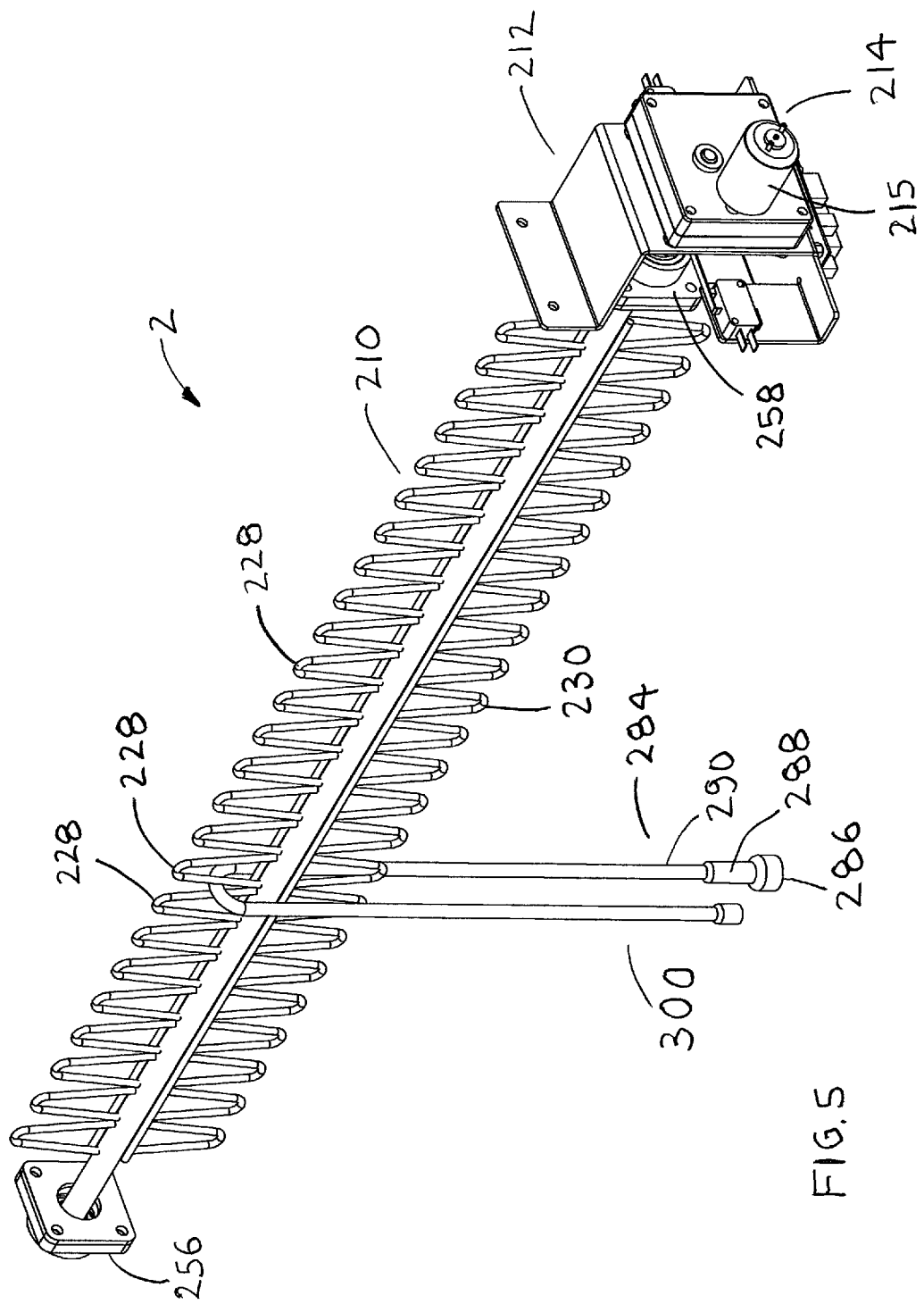
FIG. 5 is a perspective view of a pivoting cable holder in accordance with the present invention.
Figure 6:
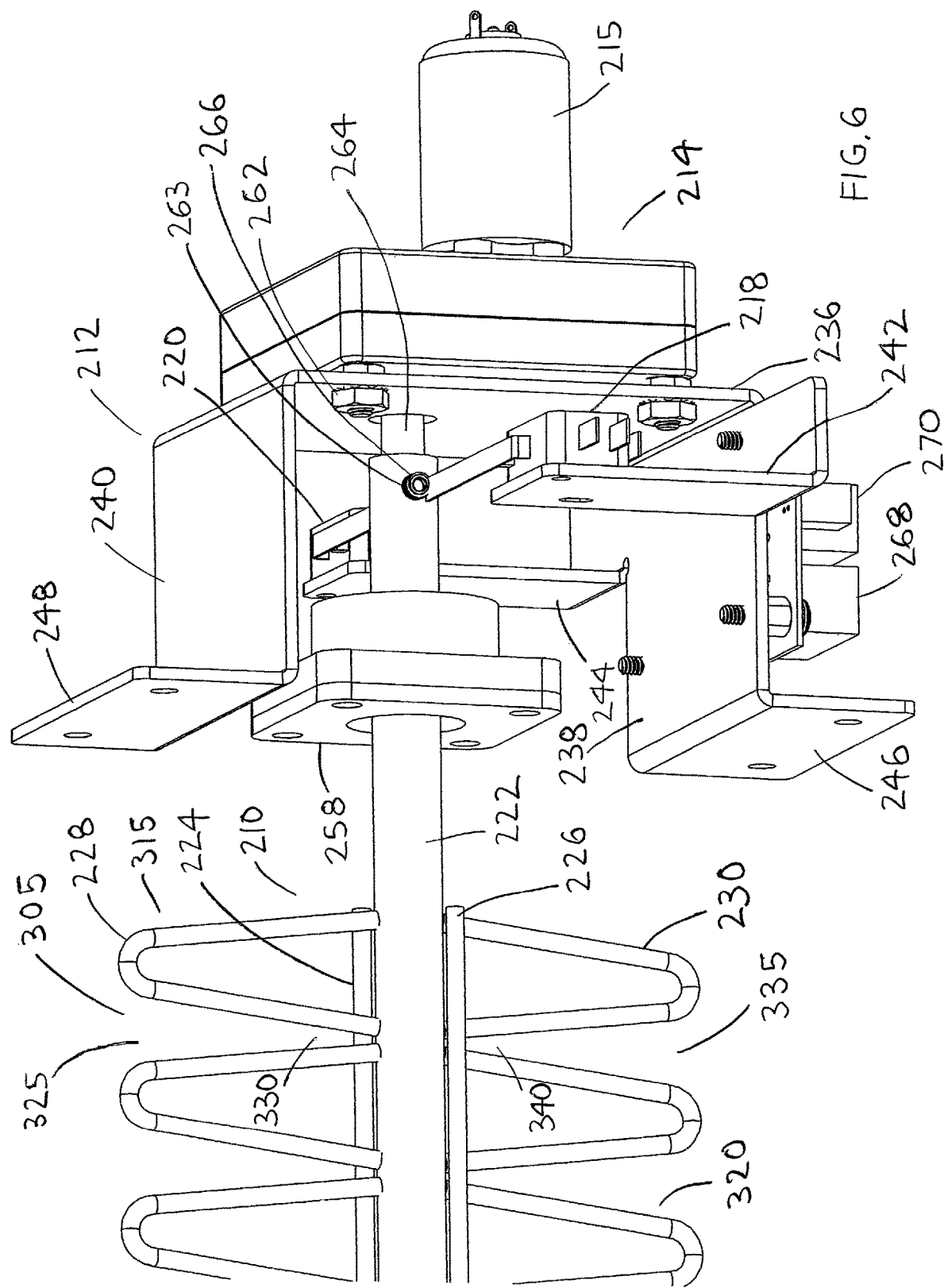
FIG. 6 is an enlarged perspective view of a mounting bracket of a pivoting cable holder in accordance with the present invention.
Figure 7:
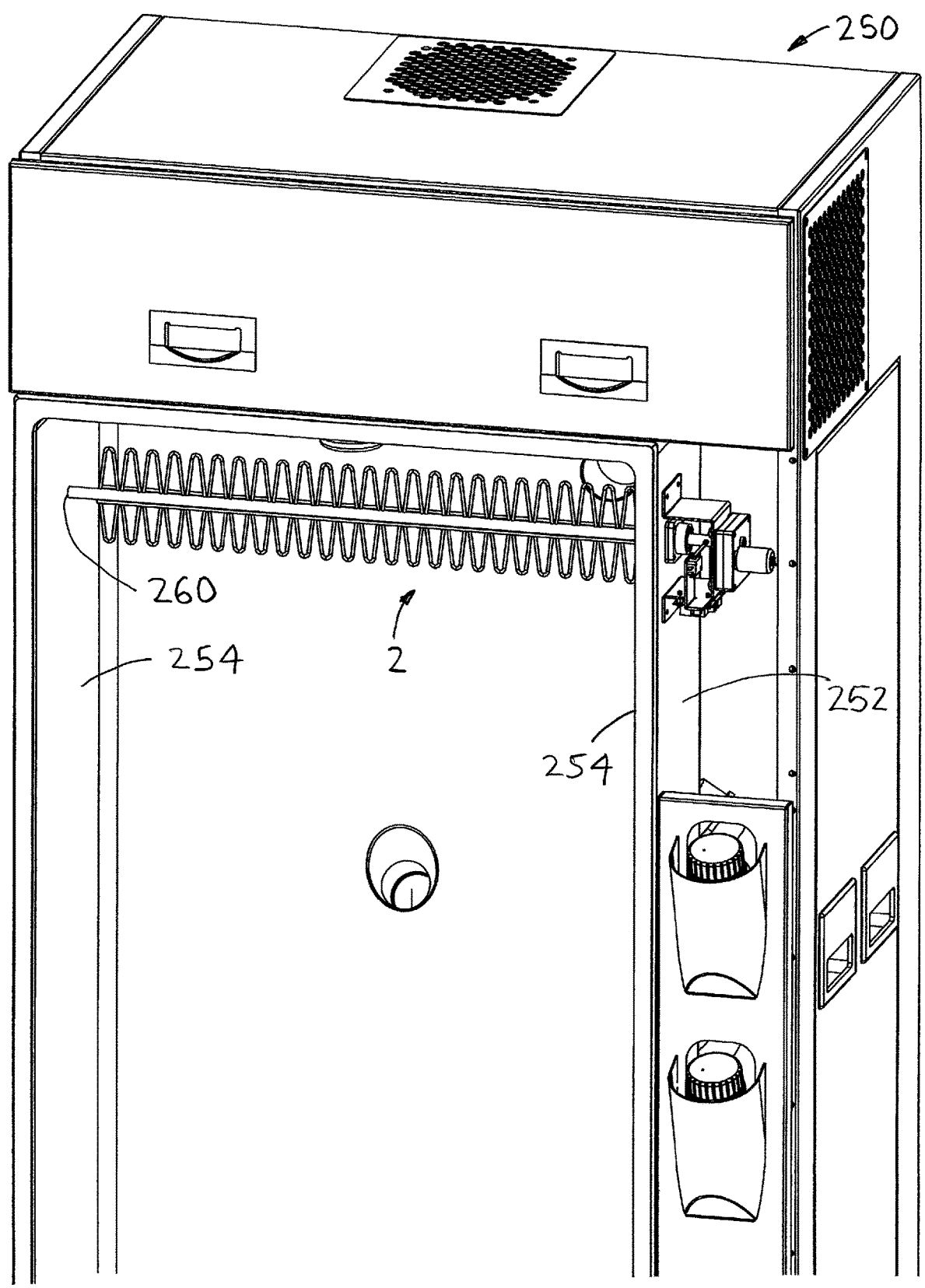
FIG. 7 is a perspective view of a pivoting cable holder mounted in a disinfection chamber of a disinfection cabinet in accordance with the present invention.

The plurality of interface test blocks 102 include an ECG interface test block, a SPO2 interface test block, a IBP interface test block, a TEMP interface test block and a TOCO interface test block. With reference to FIG. 4, each interface test block 102 preferably includes a base portion 108 and an extension portion 110, which extends from the base portion 108. When needed, the interface test block 102 will include a patient simulation device for providing feedback to a sensor of a particular cable. A plurality of connector pins (not shown) extend from a back of the base portion 108. The connector pins are plugged into one of the plurality of test sockets 98. One end of an electrical cable 112 is connected to a base socket 114 in the base portion 108 and an opposing end of the electrical cable 114 is connected to a extension socket 116 in the extension portion 110. The electronic test module 96 also tests the safety of the electrical cable 114. The electronic test module 96 is preferably located in the top equipment space 28. The inlets into the sealed test chamber 26 and the outlets from the sealed test chamber 26 are preferably sealed with check valves. HEPA filters are preferably used before the inlets and after the outlets to filter the air going into the sealed test chamber 26 and exhausting from the sealed test chamber 26.

With reference to FIGS. 5-8, a pivoting cable holder 2 preferably includes a pivoting cable tube (elongated member) 210, a mounting bracket 212, a motor with gear reduction 214, a motor controller 216, a first snap switch 218 and a second snap switch 220. The pivoting cable tube 210 preferably includes a tubular rod 222, a first mounting rod 224, a second mounting rod 226, a first plurality of V-shaped members 228 and a second plurality of V-shaped members 230. It is preferable that the retention members 228, 230 have a V-shape, but any other suitable shape may also be used. A bottom of the first plurality of V-shaped members 228 are welded to the first mounting rod 224. The first mounting rod 224 is welded to the tubular rod 222. A bottom of the second plurality of V-shaped members 230 are welded to a second mounting rod 226. The second mounting rod 226 is welded to the tubular rod 222, such that the first plurality of V-shaped members 228 are located opposite the second plurality of V-shaped members 230. The mounting bracket 212 includes a base member 236, a first leg 238, a second leg 240, a first switch plate 242 and a second switch plate 244. The first leg 238 extends outward from a first end of the base member 236 and the second leg 240 extends outward from a second end of the base member 236. The first switch plate 242 extends outward from one side of the first leg 238 and the second switch plate 244 extends from an opposite side of the first leg 238. A first mounting flange 246 extends from a bottom of the first leg 238 and a second mounting flange 248 extends from a bottom of the second leg 240.

A disinfection cabinet 250 includes a disinfection chamber 252. The disinfection chamber 252 includes opposing side walls 254. The tubular rod 222 is pivotally retained on opposing side walls 254 with a pair of flanged bearing blocks 256, 258. Tube holes 260 are formed through the opposing side walls 254 to receive the tubular rod 222. The pair of flanged bearing blocks 256, 258 are preferably retained on outside surfaces of the opposing side walls 254. The first and second snap switches 218, 220 are attached to the first and second switch plates 242, 244. The motor with gear reduction 214 is attached to the base member 236 of the mounting bracket 212 with fasteners 262. An output shaft 264 of the motor with gear reduction 214 is inserted into an end of the tubular rod 222. A threaded hole 263 is formed through an end of the tubular rod 222. A set screw 266 is threaded into the threaded hole 263. The set screw 266 is long enough to extend outward from an outer diameter of the tubular rod 222.

Figure 8:
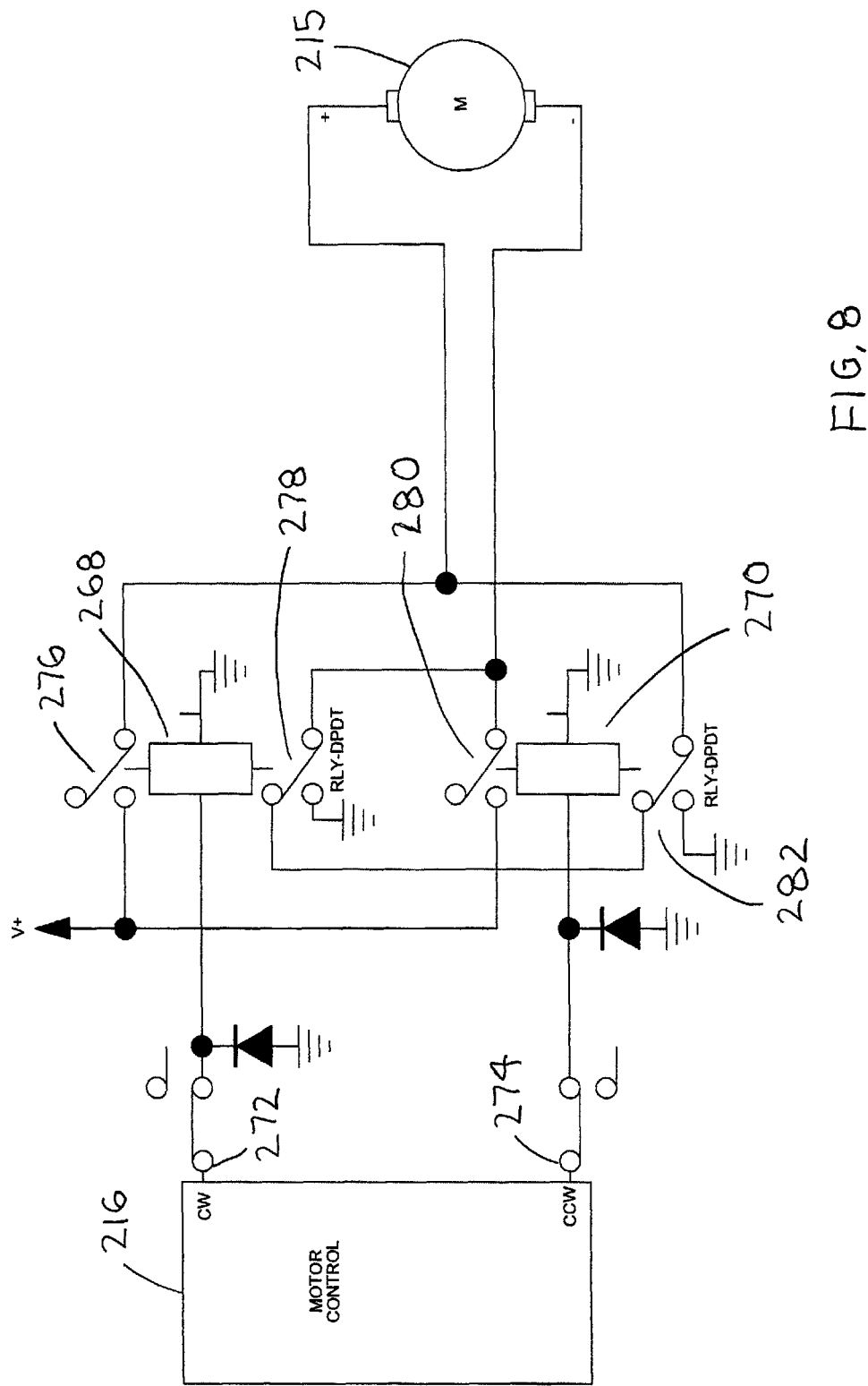
FIG. 8 is a schematic diagram of an electrical circuit for controlling rotation of a pivoting cable holder in accordance with the present invention.

With reference to FIG. 8, a clockwise DPDT relay 268 and a counter clockwise DPDT relay 270 are used to provide power to a motor 215 of the motor with gear reduction 214. The motor controller 216 includes a CW terminal 272, which outputs a clockwise voltage and CCW terminal 274, which outputs a counter clockwise voltage. The clockwise voltage is outputted for a first period of time and the counter clockwise voltage is outputted for a second period of time. The clockwise voltage is used to energize a clockwise solenoid of the clockwise DPDT relay 268, which closes a first contact 276 to supply a positive terminal of the motor 215 with the clockwise voltage and a second contact 278 to provide a ground path for a ground terminal of the motor 215. The motor 215 rotates the pivoting cable tube 210 in a clockwise direction, until the setscrew 266 forces the normally closed first snap switch 218 to open. The opening of the first snap switch 218 stops rotation of the pivoting cable tube 210. After the first period of time is over, the motor controller 216 outputs a counter clockwise voltage for a second period of time. The counter clockwise voltage is used to energize a counter clockwise solenoid of the counter clockwise DPDT relay 270, which closes a first contact 280 to supply a negative terminal of the motor 215 with the counter clockwise voltage and a second contact 282 to provide a ground path for a positive terminal of the motor 215. The pivoting cable tube 210 rotates in a counter clockwise direction, until the setscrew 266 forces the normally closed second snap switch 220 to open. The opening of the second snap switch 220 stops rotation of the pivoting cable tube 210. After the second period of time is over, the motor controller 216 outputs the clockwise voltage for a new first period of time. Each ultrasonic probe 284 (electrical device) includes an ultrasonic head 286, a handle 288 and a cord 290.

Typically, only the ultrasonic head 286 and the handle 288 are disinfected, which leaves the cord 290 untreated. The pivoting cable holder 210 enables the entire ultrasonic probe 284 to be disinfected. The cord 290 is placed between two adjacent V-shaped members 228 of the pivoting cable tube 210, such that a longer portion of the cord 290 extends from one side of the V-shaped members 228, and the ultrasonic head 286 and the handle 288 extend from an opposing side of the V-shaped members 228. The disinfection process includes a disinfection cycle, when the ultrasonic probe 284 is treated with a disinfection aerosol and a drying cycle when the disinfection aerosol is dried from the ultrasonic probe 284. The plurality of electrical devices may be dried with ambient air, heated air, vacuum or any other suitable method. The plurality of electrical devices may also be dried before the disinfection cycle. The pivoting cable tube 210 is preferably rotated 180 degrees to expose an untreated area of the cord 290 that is retained between the two adjacent V-shaped members 228 and also to dry an area of the cord 290 that is retained between the two adjacent V-shaped members 228. However, other angular rotations besides 180 degrees may also be used.

Without being limited, and with regards to FIGS. 5-8, an even more detailed description and method, is given for the current invention. Many variations and combination(s) are possible. Without being limited, one or more of any suitable and effective object(s) (300) of any suitable and effective design(s), shape(s), length(s), geometry(s), including any directly and/or indirectly part(s) and component(s), can be used in the present invention such as, but not limited to any, cable(s), data or information conduit(s), fiber optic line(s), light transferring conduit(s), hose(s), tube(s), wire(s), cord(s) (290), scope(s), ultrasonic probe(s) (284), ultrasonic probe(s) (284) attached to any cable(s) and/or any cord(s) (290), patient monitoring equipment and/or component(s), and/or electrical cable(s) (104), (Herein called "Object(s)" (300)).

First, one or more object(s) (300) is positioned into one or more of any suitable and effective treatment chamber(s) and/or test chamber(s) (26), and effectively interfaced with one or more of any suitable pivoting member(s) (315) (228) of the pivoting cable holder(s) (02), and more preferably and without limitation, any suitable and effective number of first member(s) (315) and/or one or more first v-shaped member(s) (228) (315). It is preferred, without limitation, that the first v-shaped members(s) (228) (315) are initially oriented in or close to any vertical orientation.

Without being limited, the first v-shaped members(s) (228) (315) and the second v-shaped members(s) (230) (315), and any of the open area(s) (305) (325) (335) they form, can be orientated in and/or open at, any suitable angle(s) and/or orientation(s). It is preferred, without limitation, that the first v-shaped members (228) (315) are initially located at any effective angle between about +35 degree angle and +145 degree angle, more preferably and without limitation, at any angle(s) between about +50 degree angle to +130 degree angle, and even more preferably and without limitation, about 90 degree angle and/or about vertical.

It is preferred, without limitation, that the one or more object(s) (300) can be effectively and removably interfaced with these open v-shaped open area(s) (305) (325) (335) formed by the v-shaped member(s) (315) (228) (230). It is preferred, without limitation, that the second v-shaped members (230) are identical and/or effectively close to being identical, to the first v-shaped members (228). Without being limited, one or more of any pivoting cable holder(s) (02) can be suitably and effectively located and used within any treatment chamber(s) and/or test chamber(s) (26).

Without being limited, the various member(s) (315) (228) (230), can be used for purposes including, but not limited to, holding, griping, and supporting, the one or more object(s) (300), preferably in a removable manner. Also without being limited, the one or more, but preferably a plurality, of member(s) (315) (228) (230), can be one or more of any suitable and effective size(s), length(s), width(s), shape(s), and/or geometry(s), and can be oriented in one or more of any suitable and effective, orientation(s) and/or angle(s). For example, various member(s) and/or structural protrusion(s) (Herein called "Member(s)" (315)), can be combined in a manner known to those skilled in the art, to form any effective means, structure(s), and/or shape(s), for holding the various object(s) (300) such as, but not limited to any, fork shape(s), "H" shape(s), and/or inverted arch shape(s), but at least in a manner and design, so they can hold, capture, and/or release, one or more of any object(s) (300) at any suitable and effective time(s).

It is preferred, without limitation, that the member(s) (315) (228) (230) are combined to form any suitable and effective "V" shape(s), and the open space(s) and/or area(s) (305) formed within the open V-shaped area(s) between the member(s) (315) (228) (230) are suitably and effectively sized to capture and removably hold the object(s). Without being limited, the members (315) (228) (230) that hold and/or support the object(s) (300) should at least be designed so that the various object(s) (300) and/or any parts of the object(s) (300) can be easily transferred between, preferably and without limitation, back and forth between, the first one or more v-shaped member(s) (228) (315) and the second one or more v-shaped member(s) (230) (315). The member(s) (315) can be constructed from any suitable and effective material(s). It is preferred, without limitation, that the various member(s) and more particularity, any of the v-shaped member(s), are constructed from stainless steel that is polished.

Without being limited, various attributes related to the member(s) (315) (228) (230), and any related part(s) and component(s), such as, but not limited to any, shape(s), material(s) used for part fabrication, geometry, and/or size(s), are important, especially when the pivoting cable holder(s) (02), or more particularly when the v-shaped member(s) (228) (230) and/or any other suitable and effective combination(s) and design(s) of the member(s) (315), are effectively moved, pivoted, holding and/or supporting the object(s) (300), and/or passing the object(s) (300) from one or more first member(s) (315) or first v-shaped member(s) (228) to one or more second member(s) (315) or second v-shaped member(s) (230). However, and without limitation, another important attribute for the effective operation of the pivoting cable holder (02) and effective processing, drying, and treatment(s), of the surface(s) of the object(s) (300), is the distance(s) between the various part(s) and surface(s) that are used to interface with, hold, support, release, and/or pass the object(s) (300) back and forth between the first member(s) (315) (228) and the second member(s) (315) (230) (Herein called "Holding Surface(s)" (320), which are preferably and without limitation, at least effective. Without being limited, the holding surface(s) (320) can also include the various surface(s) of any member(s) (315) that touch and contact the object(s) (300) when they are held by the one or more member(s) (315).

Without being limited, it is preferred, that the distance between the holding surface(s) (320) of the first member(s) (315) (228) and the holding surface(s) of the second member(s) (315) (230), is at least 0.25 inches or more, it is more preferred, that the distance between the holding surface(s) (320) of the first member(s) (315) (228) and the holding surface(s) of the second member(s) (315) (230), is at least one inch or more, it is even more preferred, that the distance between the holding surface(s) (320) of the first member(s) (315) (228) and the holding surface(s) of the second member(s) (315) (230), is at least two inches or more, and it is very preferred that the distance between the holding surface(s) (320) of the first member(s) (315) (228) and the holding surface(s) of the second member(s) (315) (230), is at least three inches or more.

The movement and transfer of the one or more object(s) (300) from the first one or more member(s) (315) (228) to the second one or more members (315) (230) occurs by pivoting the various v-shaped members (228) (230) any effective, distance(s), angle(s), and/or orientation(s). Without being limited, an important difference between the prior art and the present invention, is that in the present invention, the one or more member(s) (315) (228) (230) that are used to releasably hold and/or support, the object(s) (300) as they are passed from one or more first member(s) (315) (228) to one or more second member(s) (315) (230), are pivoted and/or moved in one or more of any effective lateral, circular, and/or angled upward and/or angled downward motion(s) and/or direction(s), instead of being moved vertically, or close to vertically, in an up and down motion.

It is preferred, without limitation, that the object(s) (300) are passed from the first member(s) (315) (228) to the second member(s) (315) (230) as both the first member(s) (315) (228) and the second member(s) (315) (230) effectively rotate about equally around a common point, for an effective distance and/or an effective angle of movement(s), to cause the object(s) (300) to pass from the first member(s) (315) (228) to the second member(s) (315) (230). It is also preferred, without limitation, that the object(s) (300) are passed back from the second member(s) (315) (230) back to the first member(s) (315) (228) as both the second member(s) (315) (230) and the first member(s) (315) (228) effectively rotate back about equally around a common point, for an effective distance and/or an effective angle of movement(s), to cause the object(s) (300) to pass back from the second member(s) (315) (230) back to the first member(s) (315) (228). This can be repeated for any number of effective time(s) for any of the step(s) used to treat and dry the surface(s) of the object(s) (300).

More particularly, and without limitation, it is preferred that the distance(s) between the first member(s) (315) and the second member(s) (315), and/or the first v-shaped members (228) and the the second v-shaped members (230), and/or the distance(s) between the first open area(s) (325) and the second open area(s) (335), and/or the distance(s) between the first junction(s) (330) and the second junction(s) (340), are the same and/or about the same. It is also preferred, without limitation, that the second member(s) (315) and/or the second v-shaped members (230) are identical to the first member(s) (315) and/or the first v-shaped members (228), and mirror them. Without being limited, it is also preferred that the second member(s) (315) and/or the second one or more v-shaped members (230) are positioned opposite and opposed to the first member(s) (315) and/or the one or more v-shaped member(s) (228), on the same plane.

Without being limited, it is also preferred, that the object(s) (300) can be effectively passed from any first support(s) and/or holding member(s) (315) (228) to any second support(s) and/or holding member(s) (315) (230), in any effective manner, speed, and/or rate of travel, so that any shadowed and/or covered surface(s) from any contact and/or interfacing with the first and/or second support member(s) (315) (228) (230), do not touch any surface(s), and are able to be effectively treated when moved to any of the opposite and/or alternate one or more member(s) (315).

Once the treatment chamber(s) and/or test chamber(s) (26), is effectively closed and/or sealed, the object(s) (300) can first be effectively dried, if desired and/or needed, using any suitable and effective means to treat and dry the atmosphere(s) and/or any surface(s) within the treatment chamber(s) and/or test chamber(s) (26) including any object(s) (300) surface(s), such as, but not limited to any, dehumidified air/gas(s), heated air/gas(s), fresh air/gas(s) flowed through the treatment chamber(s) and/or test chamber(s) (26), negative pressure(s), and/or vacuum, for any effective number of time(s), and for any effective duration of time(s).

Without being limited, during this pre-drying step(s), surfaces of the object(s) (300) are effectively dried while the object(s) (300) are interfaced with the first member(s) (315) and/or the one or more first v-shaped member(s) (315) (228). After the surface(s) of the object(s) (300) are effectively dry, the object(s) (300) are then transferred over to, and then interfaced with, the second member(s) (315) and/or the one or more second v-shaped member(s) (315) (230). Preferably, and without limitation, this effectively exposes any, shadowed surface(s), undried surface(s), and/or unprocessed surface(s), and/or any surface(s) of the object(s) (300) that may have been in contact with the first member(s) (315) and/or the one or more first v-shaped member(s) (228), to the atmosphere, heated air/gas(s), dehumidified air/gas(s), drying air/gas(s), negative pressure atmosphere, and/or vacuum, within the treatment chamber(s) and/or test chamber(s) (26). Without being limited, this transfer of the object(s) (300) between the various holding member(s) (315) (228) (230), can happen one or more time(s) for each processing, drying, and/or treatment step(s), and for any effective quantity of time(s), and for any effective duration of time(s).

After any pre-treatment and/or drying step(s), any one or more of any surface(s) such as, but not limited to, any, object(s) (300) surface(s), and/or surface(s) within any treatment chamber(s) and/or test chamber(s) (26), can then be treated with one or more of any suitable and effective means for any suitable and effective, treatment, cleaning, decontamination, sanitization, disinfection, high level disinfection and/or sterilization, of the various surface(s) within the the treatment chamber(s) and/or test chamber(s) (26), such as, but not limited to any, vapor(s), gas(s), UV light(s), and/or aerosol(s) (Herein called "Surface Treatment(s)". It is preferred, without limitation, that the said surface(s) are treated with any effective aerosol(s), and even more preferred, and without limitation, any aerosol(s) and/or vapor(s) formed from an aqueous solution containing peroxyacetic acid, all in a manner known to those skilled in the art.

Without being limited, during this surface treatment(s) step(s) using the one or more said means for treating the various surface(s) within the treatment chamber(s) and/or test chamber(s) (26), the surfaces of the object(s) (300) are effectively treated, preferably with any effective aerosol(s) and/or vapor(s), while the object(s) (300) are interfaced with the first one or more member(s) (315) and/or first v-shaped member(s) (228). After the surface(s) of the object(s) (300) are effectively treated, for any effective duration of time(s), the object(s) (300) are then transferred over to, and then interfaced with, the second one or more member(s) (315) and/or the second v-shaped member(s) (230). Preferably, and without limitation, this effectively exposes any surface(s) that are, shadowed surface(s), untreated surface(s), unprocessed surface(s), and/or any surface(s) of the object(s) (300) that may have been in contact with the first one or more member(s) (315) and/or the first v-shaped member(s) (228) and/or any other surface(s), to the atmosphere within the treatment chamber(s) and/or test chamber(s) (26). Without being limited, the object(s) (300) can be transferred back and forth between the the first member(s) (315) and/or the first one or more v-shaped member(s) (228), and the second member(s) (230) and/or the second one or more v-shaped member(s) (230), any number of time(s) and for any duration of time(s), to expose all of the surface(s) of the object(s) (300) and/or all of the object(s) (300) surface(s) targeted for effective treatment, to the surface treatment(s), for any suitable and effective, treatment outcome(s) and result(s).

Without being limited, the object(s) (300) can also be dried after each time they are treated in their respective first or second member(s) (315) and/or v-shaped member(s) (228) (230), or after they have been moved to one or more new or different member(s) and/or v-shaped member(s) (228) (230), and before they are treated by any surface treatment(s) at these alternate, new, and/or returning location(s).

It is also preferred, without limitation, that after the one or more treatment step(s) is effectively completed, the object(s) (300) are returned back to the first member(s) (315) and/or the first one or more v-shaped member(s) (228) before any final drying step(s) are completed.

After the effective treatment of any, but preferably all, of the object(s) (300) surface(s), and/or any surfaces within the treatment chamber(s) and/or test chamber(s) (26), any, but preferably all, of the object(s) surface(s) and/or the surface(s) within the treatment chamber(s) and/or test chamber(s) (26), can be effectively dried, using any suitable and effective means to treat and dry the atmosphere(s) and/or any surface(s) within the treatment chamber(s) and/or test chamber(s) (26) including any object(s) (300) surface(s), such as, but not limited to any, dehumidified air/gas(s), heated air/gas(s), fresh and/or heated air/gas(s) flow through the treatment chamber(s) and/or test chamber(s) (26), negative pressure(s), and/or vacuum, for any suitable and effective time(s) and/or duration of time(s).

It is preferred, without limitation, that at least heated air/gas(s), using effectively filtered fresh air from outside of the the treatment chamber(s) and/or test chamber(s) (26), that is effectively heated before it is flowed through the the treatment chamber(s) and/or test chamber(s) (26), is used to effectively dry the surface(s) within. The air/gas(s) can be heated to any suitable and effective temperature(s), preferably and without limitation, at least any effective temperature(s) between 70 to 200 degree Fahrenheit, and even more preferably, and without limitation, any temperature(s) between 90-120 degree Fahrenheit. It is preferred, without limitation, that if any chemicals were used to treat the various surface(s) within the treatment chamber(s) and/or test chamber(s) (26), the heated air/gas(s) that are flowed through the treatment chamber(s) and/or test chamber(s) (26), are effectively filtered after they leave the treatment chamber(s) and/or test chamber(s) (26), and before they are removed from the entire treatment apparatus and/or machine and into the surrounding environment.

Without being limited, during this drying step(s), surfaces of the object(s) (300) are effectively dried while the object(s) (300) are interfaced, preferably and without limitation, with the first one or more member(s) (315) and/or the first v-shaped member(s) (228). After the surface(s) of the object(s) (300) are effectively dry, the object(s) (300) are then transferred over to, and then interfaced with, the second one or more member(s) (315) and/or the second v-shaped member(s) (230). Preferably, and without limitation, this effectively exposes any, shadowed surface(s), undried surface(s), and/or unprocessed surface(s), and/or any surface(s) of the object(s) (300) that may have been in contact with the first one or more member(s) and/or first v-shaped member(s) (228), to the atmosphere, heated air/gas(s), dehumidified air/gas(s), drying air/gas(s), negative pressure atmosphere, and/or vacuum, within the treatment chamber(s) and/or test chamber(s) (26). Without being limited, this transfer of the object(s) (300) between the various holding member(s) (228) (230) (315), can happen one or more time(s), and for any effective duration of time(s).

Also without being limited, after the various surface(s) within the treatment chamber(s) and/or test chamber(s) (26), are effectively dry, and the drying step(s) are completed, the atmosphere(s) within the treatment chamber(s) and/or test chamber(s) (26), can also be purged if needed, with fresh air that is preferably and without limitation, effectively filtered before it enters the treatment chamber(s) and/or test chamber(s) (26), and is also effectively filtered before it is exhausted into the surrounding environment, until any chemical concentration(s) inside the treatment chamber(s) and/or test chamber(s) (26), are reduced to any suitable and effective level(s), all in a manner known to those skilled in the art.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of at least one of sanitizing, disinfecting, high level disinfecting and sterilization of a plurality of objects, comprising the steps of:
providing an elongated member having a plurality of V-shaped retention members for retaining the plurality of objects, an open portion of said plurality of V-shaped retention members is attached directly to said elongated member to form a plurality of V-shaped slots, said elongated member is retained inside a treatment cabinet on a horizontal axis, the plurality of objects are retained between said plurality of V-shaped slots;
applying a substance to the plurality of objects during a substance cycle;
drying the plurality of objects during a drying cycle; and
rotating said elongated member in at least one of a clockwise direction and a counterclockwise direction, at least once during said substance cycle and said drying cycle.

2. The method of claim 1, further comprising the step of: drying the plurality of objects before said substance cycle.

3. The method of claim 1, further comprising the step of:
providing said elongated member with a tubular rod, a first plurality of V-shaped members and a second plurality of V-shaped members, a bottom of said first plurality of V-shaped members are attached to said tubular rod, a bottom of said second plurality of V-shaped members are attached to said tubular rod, such that said first plurality of V-shaped members are located opposite said second plurality of V-shaped members.

4. The method of claim 3, further comprising the step of:
extending a set screw from an outer diameter of said tubular rod, locating a first switch and a second switch to be actuated by said set screw during a rotation of said elongated member.

5. The method of claim 4, further comprising the step of:
providing a motor, a clockwise relay and a counter clockwise relay, said motor rotates said elongated member, said clockwise relay supplies voltage to said motor for clockwise rotation, said counter clockwise relay supplies voltage to said motor for counter clockwise rotation.

6. The method of claim 5, further comprising the step of:
attaching a bracket to said treatment cabinet, attaching said motor to said bracket, attaching said first and second switches to said bracket.

7. The method of claim 6, further comprising the step of:
providing said bracket with a base member, a first leg, a second leg, a first switch plate and a second switch plate, said first leg extends outward from a first end of said base member, said second leg extends outward from a second end of said base member, said first switch plate extends outward from one side of said first leg, said second switch plate extends from an opposite side of said first leg.

8. A method of at least one of sanitizing, disinfecting, high level disinfecting and sterilization of a plurality of objects, comprising the steps of:
providing an elongated member having a plurality of V-shaped retention members for retaining the plurality of objects, an open portion of said plurality of V-shaped retention members is attached directly to said elongated member to form a plurality of V-shaped slots, said elongated member is retained inside a treatment cabinet on a horizontal axis, the plurality of objects are retained between said plurality of V-shaped slots;
providing a motor for rotating said elongated member;
providing a motor controller for controlling a rotation of said motor in a clockwise and a counter clockwise direction;
applying a substance to the plurality of objects during a substance cycle; and
drying the plurality of objects.

9. The method of claim 8, further comprising the step of:
drying the plurality of objects before said substance cycle.

10. The method of claim 8, further comprising the step of:
providing said elongated member with a tubular rod, a first plurality of V-shaped members and a second plurality of V-shaped members, a bottom of said first plurality of V-shaped members are attached to said tubular rod, a bottom of said second plurality of V-shaped members are attached to said tubular rod, such that said first plurality of V-shaped members are located opposite said second plurality of V-shaped members.

11. The method of claim 10, further comprising the step of:
extending a set screw from an outer diameter of said tubular rod, locating a first switch and a second switch to be actuated by said set screw during a rotation of said elongated member.

12. The method of claim 11, further comprising the step of:
providing a clockwise relay and a counter clockwise relay, said motor rotates said elongated member, said clockwise relay supplies voltage to said motor for clockwise rotation, said counter clockwise relay supplies voltage to said motor for counter clockwise rotation.

13. The method of disinfecting a plurality of electrical devices of claim 12, further comprising the step of:
attaching a bracket to said treatment cabinet, attaching said motor to said bracket, attaching said first and second switches to said bracket.

14. The method of claim 13, further comprising the step of:
providing said bracket with a base member, a first leg, a second leg, a first switch plate and a second switch plate, said first leg extends outward from a first end of said base member, said second leg extends outward from a second end of said base member, said first switch plate extends outward from one side of said first leg, said second switch plate extends from an opposite side of said first leg.

15. A method of at least one of sanitizing, disinfecting, high level disinfecting and sterilization of disinfecting a plurality of objects, comprising the steps of:
providing an elongated member having a plurality of V-shaped retention members for retaining the plurality of objects, an open portion of said plurality of V-shaped retention members is attached directly to said elongated member to form a plurality of V-shaped slots, said elongated member is retained inside a disinfection cabinet on a horizontal axis, the plurality of objects are retained between said plurality of V-shaped slots;
providing a motor for rotating said elongated member;
providing a motor controller for controlling a rotation of said motor;
applying a substance to the plurality of objects during a substance cycle, rotating said elongated member in at least one of a clockwise direction or a counter clockwise direction, at least once during said substance cycle; and
drying the plurality of objects, rotating said elongated member in at least one of a counter clockwise direction or a clockwise direction at least once during a drying cycle.

16. The method of claim 15, further comprising the step of:
drying the plurality of objects before said substance cycle.

17. The method of claim 15, further comprising the step of:
providing said elongated member with a tubular rod, a first plurality of V-shaped members and a second plurality of V-shaped members, a bottom of said first plurality of V-shaped members are attached to said tubular rod, a bottom of said second plurality of V-shaped members are attached to said tubular rod, such that said first plurality of V-shaped members are located opposite said second plurality of V-shaped members.

18. The method of claim 17, further comprising the step of:
extending a set screw from an outer diameter of said tubular rod, locating a first switch and a second switch to be actuated by said set screw during a rotation of said elongated member.

19. The method of 18, further comprising the step of:
providing a clockwise relay and a counter clockwise relay, said motor rotates said elongated member, said clockwise relay supplies voltage to said motor for clockwise rotation, said counter clockwise relay supplies voltage to said motor for counter clockwise rotation.

20. The method of claim 19, further comprising the step of:
attaching a bracket to said disinfection cabinet, attaching said motor to said bracket, attaching said first and second switches to said bracket.

* * * * *